US010969448B2

(12) United States Patent
Menteur et al.

(10) Patent No.: US 10,969,448 B2
(45) Date of Patent: Apr. 6, 2021

(54) MAGNETIC RESONANCE IMAGING (MRI) APPARATUS AND CRYOSTAT FOR MRI APPARATUS

(71) Applicant: KONINKLIJKE PHILIPS N.V., Eindhoven (NL)

(72) Inventors: Philippe Abel Menteur, Eindhoven (NL); Joshua Kent Hilderbrand, Eindhoven (NL); Glen George Pfleiderer, Eindhoven (NL); Gregg Orville Kimball, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 370 days.

(21) Appl. No.: 15/777,999

(22) PCT Filed: Nov. 17, 2016

(86) PCT No.: PCT/IB2016/056910
§ 371 (c)(1),
(2) Date: May 22, 2018

(87) PCT Pub. No.: WO2017/089929
PCT Pub. Date: Jun. 1, 2017

(65) Prior Publication Data
US 2018/0348318 A1 Dec. 6, 2018

Related U.S. Application Data

(60) Provisional application No. 62/259,758, filed on Nov. 25, 2015.

(51) Int. Cl.
*G01R 33/38* (2006.01)
*G01R 33/3815* (2006.01)
(Continued)

(52) U.S. Cl.
CPC .......... *G01R 33/3804* (2013.01); *A61B 5/055* (2013.01); *G01R 33/3815* (2013.01); *G01R 33/3856* (2013.01); *H01F 6/04* (2013.01)

(58) Field of Classification Search
CPC ................ G01R 1/00; H01F 1/00; A61B 1/00
See application file for complete search history.

(56) References Cited

U.S. PATENT DOCUMENTS 4,782,671 A  11/1988  Breneman et al.
2006/0022779 A1  1/2006  Jiang et al.
(Continued)

FOREIGN PATENT DOCUMENTS

EP  1808706 A1  7/2007
JP  0121410 A  11/1989
(Continued)

*Primary Examiner* — Jermele M Hollington
*Assistant Examiner* — Temilade S Rhodes-Vivour

(57) ABSTRACT

An apparatus (100) includes: an outer shell (211); an inner vessel (212) disposed within the outer shell; a cold head (260) having a first stage (261) disposed within the outer shell, and having a second stage (262) for contacting an interior of the inner vessel; a vent (215) extending from the interior of the inner vessel to the exterior of the outer shell; first and second heat exchangers (302a, 302b); a first thermal shield (213) disposed between the inner vessel and the outer shell; and a second thermal shield (214) disposed between the inner vessel and the first thermal shield. The first thermal shield is thermally connected to the first stage of the cold head and the first heat exchanger and is thermally isolated from the inner vessel and outer shell. The second thermal shield is thermally connected to the second heat exchanger and is thermally isolated from the inner vessel, outer shell, first thermal shield, and cold head.

20 Claims, 5 Drawing Sheets

(51) Int. Cl.
   *H01F 6/04*        (2006.01)
   *A61B 5/055*       (2006.01)
   *G01R 33/385*      (2006.01)

(56) References Cited

U.S. PATENT DOCUMENTS

| | | |
|---|---|---|
| 2008/0155995 A1 | 7/2008 | Hughes et al. |
| 2009/0275476 A1 | 11/2009 | Atrey |
| 2009/0279260 A1 | 11/2009 | Yu |
| 2012/0176134 A1* | 7/2012 | Jiang ............... G01R 33/3804 324/318 |
| 2013/0045870 A1* | 2/2013 | Rogers ............... B65D 88/741 505/163 |
| 2013/0157865 A1* | 6/2013 | Shen ............... G01R 33/3804 505/162 |
| 2014/0061202 A1* | 3/2014 | Mathieu ............ G01R 33/3804 220/560.09 |
| 2014/0155268 A1* | 6/2014 | Shen ............... G01R 33/387 505/162 |
| 2015/0196221 A1* | 7/2015 | Garside ............... A61B 5/055 600/410 |

FOREIGN PATENT DOCUMENTS

| | | |
|---|---|---|
| JP | 03129784 A | 6/1991 |
| JP | 10177914 A | 6/1998 |
| JP | 2009273673 A | 11/2009 |

\* cited by examiner

MAGNETIC RESONANCE IMAGING (MRI) APPARATUS AND CRYOSTAT FOR MRI APPARATUS

CROSS REFERENCE TO RELATED APPLICATIONS

This application is a U.S. national phase application of International Application No. PCT/IB2016/056910, filed on Nov. 17, 2016, which claims the benefit of U.S. provisional Application Ser. No. 62/259,758 filed on Nov. 25, 2015 and is incorporated herein by reference.

TECHNICAL FIELD

The present invention generally pertains to a magnetic resonance imaging (MRI) apparatus and a cryostat for cooling superconducting coils for a magnet of an MRI apparatus.

BACKGROUND AND SUMMARY

Superconducting magnet systems are used in a variety of contexts, including nuclear magnetic resonance (NMR) analysis, and magnetic resonance imaging (MRI). To realize superconductivity, a magnet is maintained in a cryogenic environment at a temperature near absolute zero. Typically, the magnet system includes one or more electrically conductive coils operating as one or more magnets and which are disposed in a cryostat and cooled by a cryogenic fluid such as liquid helium to maintain superconductivity. The cryogenic fluid is in turn cooled by a refrigeration unit which includes a compressor which drives a cooling unit or "cold head" in order to maintain the temperature in the cryostat to be near absolute zero so that the conditions for the magnet's superconductivity persist.

However, during transportation of the cryostat, for example, the refrigeration system is typically not powered. In that case, the temperature of the cryogenic fluid within the cryostat will begin to rise. If power is not supplied to the refrigeration system for an extended period, such as may be the case during transport, this will eventually cause some or all of the cryogenic fluid to evaporate and be lost, for example through a vent or pressure relieve valve that is typically included in the superconducting magnet system. Indeed if the transportation time is too long, then the entire inventory of liquid helium can be lost. A cryostat with a high rate of helium loss can present difficult logistical challenges, because the transportation times must be managed carefully so that the helium inventory is not fully depleted resulting in a warm helium vessel upon arrival, which can be a complex and expensive issue to resolve at the destination site.

Furthermore, it is possible after system installation that the refrigeration system may become non-operational, for example due to a malfunction of the compressor, or due to a loss of AC Mains power for operating the compressor, thereby shutting down refrigeration of the superconducting magnet system. When power is no longer supplied to the compressor and the cold head ceases to cool the cryogenic fluid, conditions within the cryostat degrade and the temperature of the magnet will begin to rise. At a certain point, if power is not reapplied to restore cooling of the magnet's environment, then the magnet's temperature will rise to reach the so-called critical temperature where the magnet will "quench" and convert its magnetic energy to heat energy, thereby heating the cryogenic fluid within the cryostat. This, again, may cause some or all of the cryogenic fluid to evaporate and be lost through the vent or pressure relieve valve. Furthermore, the heat may damage the magnet and/or other components of the apparatus.

In that case, once power is restored, to return the magnet to superconducting operation may require replacing the lost cryogenic fluid within the cryostat, then cooling the magnet back down to below the critical temperature, connecting leads to the magnet to reapply current from an external power supply to the magnet so as to regenerate the magnetic field, and then disconnecting the magnet from the external power supply again. Furthermore, if heat from the quench caused the magnet or other components to be damaged, they may need to be repaired or replaced.

This recovery process can be expensive and time-consuming. Typically a trained technician must be dispatched to the facility (e.g., a medical center or hospital) where the superconducting magnet system is located and new cryogenic fluid (e.g. liquid helium), which may be quite costly, must be supplied to the cryostat to make up for what was lost during the quench.

Accordingly, it would be desirable to provide a cryostat which may exhibit a reduced rate of loss of the cryogenic material (e.g., helium) in the case of a loss of refrigeration due to transport, power loss, or malfunction.

In one aspect of the present invention, a magnetic resonance imaging (MRI) apparatus comprises: a patient table configured to hold a patient; a superconducting electrically conductive coil configured to produce a magnetic field when an electrical current is passed therethrough; gradient coils configured to at least partially surround a portion of the patient for which the MRI apparatus generates an image; a radio frequency (RF) coil configured to apply an RF signal to the portion of a patient and to alter an alignment of the magnetic field; a sensor configured to detect changes in the magnetic field caused by the radio frequency signal and the patient; an outer shell; an inner vessel disposed within the outer shell, the inner vessel having disposed therein the superconducting electrically conductive coil and being configured to have a cryogenic fluid disposed therein; a cold head having: a first cooling stage which is disposed within the outer shell and which is configured to provide cooling to a first temperature, and having a second cooling stage which is disposed within the outer shell and which is configured to contact the cryogenic fluid within the inner vessel and cool the cryogenic fluid to a second temperature which is less than the first temperature; a vent extending from an interior of the inner vessel to an exterior of the outer shell, the vent having associated therewith a first heat exchanger and a second heat exchanger; a first thermal shield disposed between the inner vessel and the outer shell, the first thermal shield being thermally connected to the second cooling stage of the cold head and further being thermally connected to the first heat exchanger and being thermally isolated from the inner vessel and outer shell, wherein a first vacuum space is defined between the first thermal shield and the outer shell; a second thermal shield disposed between the inner vessel and the first thermal shield, the second thermal shield being thermally connected to the second heat exchanger and being thermally isolated from the inner vessel, the outer shell, the first thermal shield, and the cold head, wherein a second vacuum space is defined between the first thermal shield and the second thermal shield, and a third vacuum space is defined between the first thermal shield and the inner vessel; and a plurality of thermally isolating support elements configured to attach the inner vessel, the outer shell, the first thermal shield, and the second thermal shield to each other.

In some embodiments, the plurality of thermally isolating support elements are made of one selected from Kevlar, s-glass/epoxy, G-10, carbon fiber/epoxy, and alumina.

In some embodiments, the plurality of thermally isolating support elements further comprise: at least one first thermally isolating support element physically connecting the inner vessel, the second thermal shield, and the outer shell to each other; and at least one second thermally isolating support element physically connecting the first thermal shield and the second thermal shield to each other, wherein the first thermal shield and the second thermal shield are both thermally attached to the at least one first thermally isolating support element.

In some embodiments, the plurality of thermally isolating support elements further comprise: at least one first thermally isolating support element physically connecting the inner vessel, the first thermal shield, and the outer shell to each other; and at least one second thermally isolating support element physically connecting the first thermal shield and the second thermal shield to each other, wherein the first thermal shield and the second thermal shield are both thermally attached to the at least one first thermally isolating support element.

In some embodiments, the plurality of thermally isolating support elements further comprise: at least one first thermally isolating support element physically connecting the inner vessel, the first thermal shield, and the outer shell to each other; and at least one second thermally isolating support element physically connecting the first thermal shield and inner vessel to each other, wherein the first thermal shield and the second thermal shield are both thermally attached to the at least one first thermally isolating support element.

In some embodiments, the cold head is welded to the outer shell.

In some embodiments, the inner vessel has the cryogenic fluid disposed therein as liquid helium.

In some versions of these embodiments, a helium gas passes through the vent from the inner vessel to outside of the outer shell after a period of time when the cold head is not powered.

In some embodiments, the first temperature is in a range of 35° K to 75° K, and the second temperature is below 5° K.

In some embodiments, the plurality of thermally isolating support elements includes at least one flexible support element.

In another aspect of the present invention, an apparatus comprises: an outer shell; an inner vessel disposed within the outer shell, the inner vessel having disposed therein an electrically conductive coil; a cold head having a first cooling stage disposed within the outer shell, and having a second cooling stage disposed within the outer shell and configured to contact an interior space inside the inner vessel; a vent extending from the interior of the inner vessel to an exterior of the outer shell, the vent having associated therewith a first heat exchanger and a second heat exchanger; a first thermal shield disposed between the inner vessel and the outer shell, the first thermal shield being thermally connected to the second cooling stage of the cold head and further being thermally connected to the first heat exchanger and being thermally isolated from the inner vessel and outer shell; and a second thermal shield disposed between the inner vessel and the first thermal shield, the second thermal shield being thermally connected to the second heat exchanger and being thermally isolated from the inner vessel, the outer shell, the first thermal shield, and the cold head.

In some embodiments, the apparatus further comprises: at least one first thermally isolating support element physically connecting the inner vessel, the second thermal shield, and the outer shell to each other; and at least one second thermally isolating support element physically connecting the first thermal shield and the second thermal shield to each other.

In some versions of these embodiments, the first thermal shield and the second thermal shield are both thermally attached to the at least one first thermally isolating support element.

In some embodiments, the apparatus further comprises: at least one first thermally isolating support element physically connecting the inner vessel, the first thermal shield, and the outer shell to each other; and at least one second thermally isolating support element physically connecting the first thermal shield and the second thermal shield to each other.

In some versions of these embodiments, the first thermal shield and the second thermal shield are both thermally attached to the at least one first thermally isolating support element.

In some embodiments, the apparatus further comprises: at least one first thermally isolating support element physically connecting the inner vessel, the first thermal shield, and the outer shell to each other; and at least one second thermally isolating support element physically connecting the first thermal shield and inner vessel to each other.

In some versions of these embodiments, the first thermal shield and the second thermal shield are both thermally attached to the at least one first thermally isolating support element.

In some embodiments, the apparatus further comprises: at least one first thermally isolating support element physically connecting the inner vessel and the second thermal shield to each other; at least one second thermally isolating support element physically connecting the first thermal shield and the second thermal shield to each other; and at least one third thermally isolating support element physically connecting the second thermal shield and the outer shell to each other.

In some embodiments, the apparatus further comprises: at least one first thermally isolating support element physically connecting the inner vessel and the first thermal shield to each other; at least one second thermally isolating support element physically connecting the first thermal shield and the second thermal shield to each other; and at least one third thermally isolating support element physically connecting the first thermal shield and the outer shell to each other.

In some embodiments, the apparatus further comprises: at least one first thermally isolating support element physically connecting the inner vessel and the first thermal shield to each other; at least one second thermally isolating support element physically connecting the first thermal shield and the inner vessel to each other; and at least one third thermally isolating support element physically connecting the first thermal shield and the outer shell to each other.

BRIEF DESCRIPTION OF THE DRAWINGS

The present invention will be more readily understood from the detailed description of exemplary embodiments presented below considered in conjunction with the accompanying drawings, in which.

DETAILED DESCRIPTION

The present invention will now be described more fully hereinafter with reference to the accompanying drawings, in which embodiments of the present invention are shown. The present invention may, however, be embodied in different forms and should not be construed as limited to the embodiments set forth herein. Rather, these embodiments are provided as teaching examples of the invention.

Figure 1:
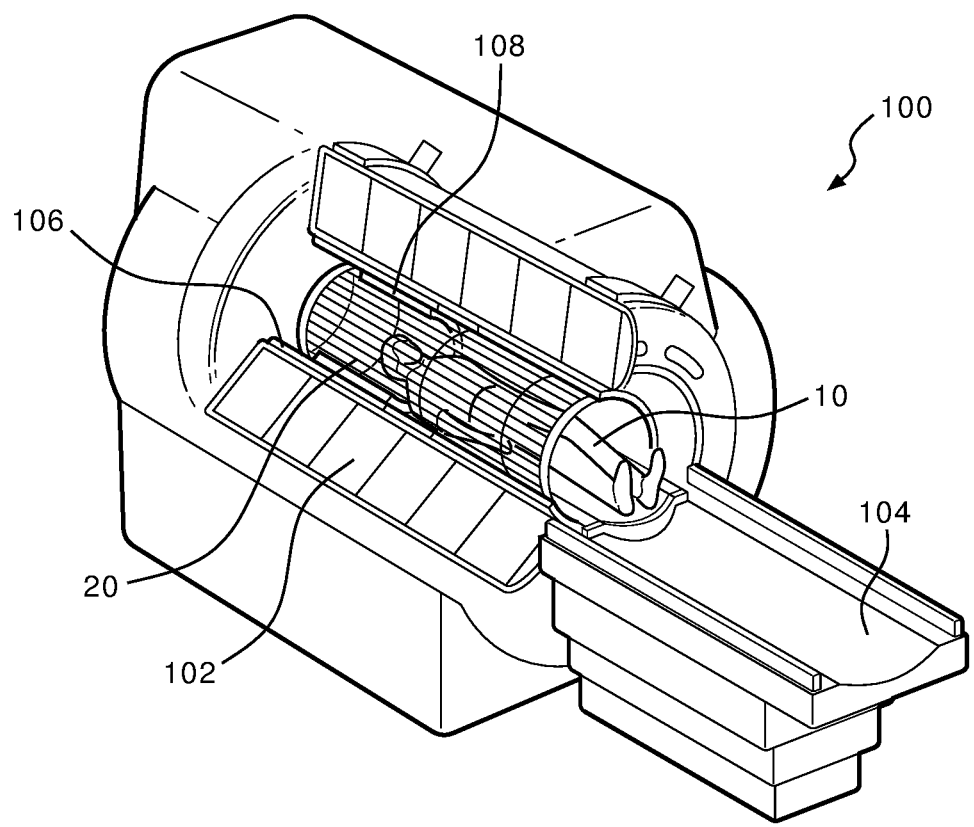
FIG. 1 illustrates an exemplary embodiment of a magnetic resonance imaging (MRI) apparatus.

FIG. 1 illustrates an exemplary embodiment of a magnetic resonance imaging (MRI) apparatus 100. MRI apparatus 100 includes a magnet system 102; a patient table 104 configured to hold a patient 10; gradient coils 106 configured to at least partially surround at least a portion of patient 10 for which MRI apparatus 100 generates an image; and a radio frequency coil 108 configured to apply a radio frequency signal to at least the portion of patient 10 which is being imaged, and to alter the alignment of the magnetic field; and a sensor 20 configured to detect changes in the magnetic field caused by the radio frequency signal and patient 10.

The general operation of an MRI apparatus is well known and therefore will not be repeated here.

In MRI apparatus 100, magnet system 102 is a superconducting magnet system which includes one or more electrically conductive coil(s) disposed within a cryostat, whereby the electrically conductive coil(s) are maintained at a very low temperature by a refrigerator or cooler and a cryogenic fluid (e.g., liquid helium) so as to be superconducting.

Cryostats referred to as zero boil-off systems may include a liquid helium vessel within the cryostat, and a single thermal shield between the liquid helium vessel and the outer enclosure of the cryostat, and this thermal shield may be thermally attached to the first cooling stage of a two-stage cold head of the refrigerator. The second cooling stage of the cold head operates at a temperature which is lower than the boiling point of the liquid helium, thereby condensing the helium vapor back into the liquid state via a heat exchanger and returning it to the liquid helium inventory in the vessel. The thermal shield attached to the first cooling stage of the cold head operates at a much higher temperature range than the second cooling stage which cools the helium within the vessel. The purpose of the thermal shield is to shunt as much heat as possible to the first cooling stage of the cold head during normal operation so that conduction of any remaining heat to the liquid helium vessel is minimized.

However, a problem with a single thermal shield system with a cold head in the vacuum space of the cryostat is that a high rate of helium loss may occur when the refrigeration system fails, or during transportation of the cryostat while the refrigeration system is not powered, as described above.

To reduce the rate of helium loss, the escaping cold helium gas may be used to cool the thermal shield via a heat exchanger, thereby reducing the temperature of the thermal shield. Unfortunately, the largest heat load to the thermal shield is the non-operational cold head, which may cause the thermal shield to operate at temperatures above 100° K where the thermal radiation to the liquid helium vessel is too high. In some cases, this may result in a rate of helium loss of much greater than 3 liquid helium liters per hour, which is undesirable.

Figure 2:
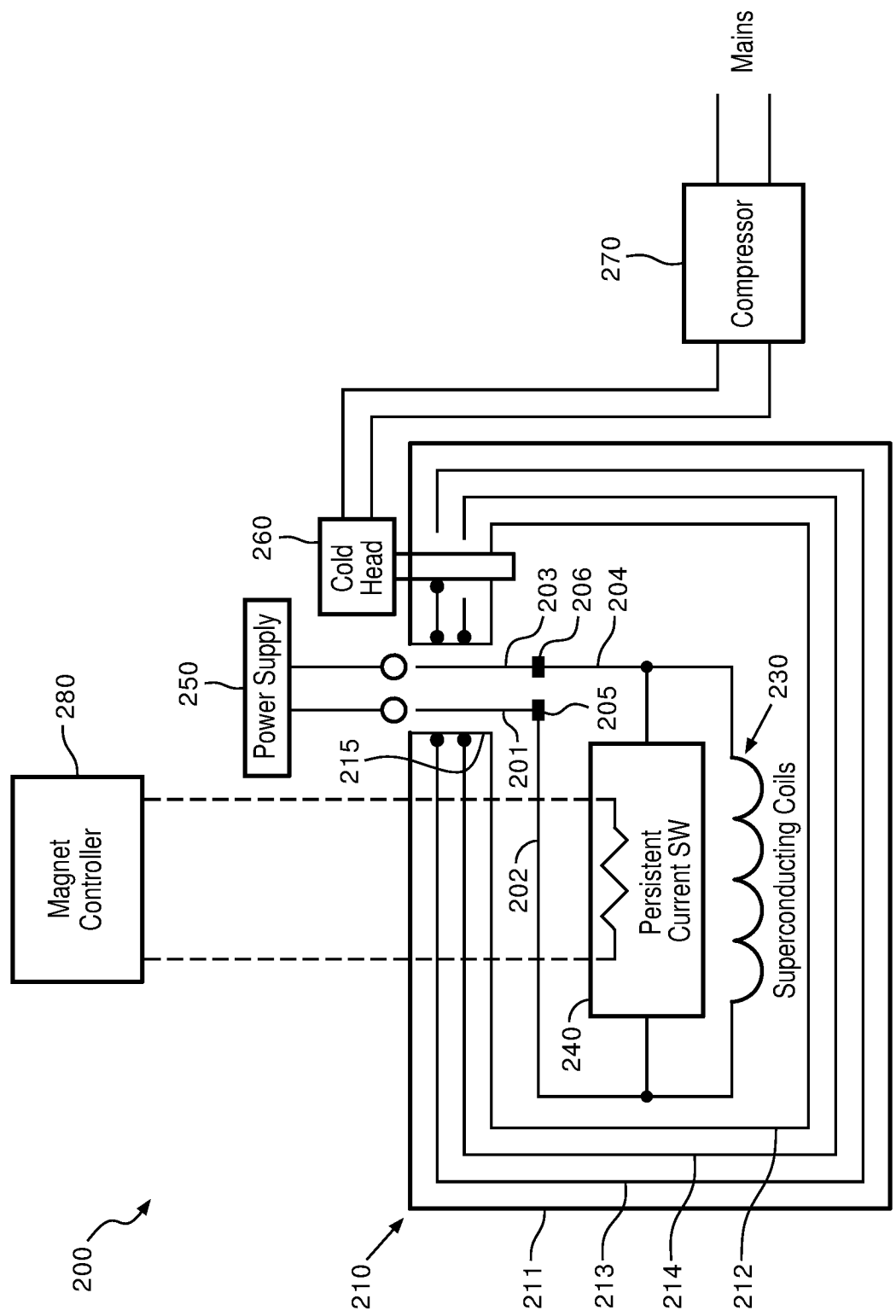
FIG. 2 is a functional diagram illustrating one example embodiment of a superconducting magnet system which may be employed in an MRI apparatus.

Accordingly, FIG. 2 illustrates one example embodiment of a superconducting magnet system 200 which may be employed in an MRI apparatus, such as MRI apparatus 100 and which includes a "floating" thermal shield which is not thermally coupled to the cold head. In particular, superconducting magnet system 200 may be one embodiment of magnet system 102 in MRI apparatus 100. It should be understood that, in general, superconducting magnet system 200 may include many other components which are not illustrated in FIG. 2. Some components have been omitted from FIG. 2 for clarity of illustration, and so as not to obscure aspects of the present invention to be discussed below.

Superconducting magnet system 200 includes a cryostat 210 having an enclosure, or outer vacuum container (hereinafter referred to as an outer shell) 211 and: a first thermal shield 213; a second thermal shield 214; and a liquid helium tank or vessel 212 (hereinafter referred to as an inner vessel) all disposed within outer shell 211. Superconducting magnet system 200 also includes a vent 215 for filling inner vessel 212 with a cryogenic fluid (e.g., liquid helium) and through which boiled off helium gas may be released from inner vessel 212 to outside of cryostat 210. Superconducting magnet system 200 further includes a cold head 260 driven by a compressor 270 to recondense helium gas in inner vessel 212. Beneficially, cold head 260 may be a two-stage cold head, as will be described in greater detail below with respect to FIG. 3. Although not shown in FIG. 2, superconducting magnet system 200 also includes heat exchangers which are associated with vent 215 and thermally attached or coupled to first and second thermal shields 213 and 214. As will be further described in greater detail below, second thermal shield 214 is a "floating" thermal shield which is not thermally coupled to the cold head 260. This and other significant details of the arrangement of the above-mentioned elements of superconducting magnet system 200 will be described in detail below with respect to FIG. 3.

Superconducting magnet system 200 also includes one or more electrically conductive coil(s) 230 and a persistent current switch 240 disposed within a cryogenic fluid (e.g., liquid helium) in liquid helium vessel 212 of cryostat 210, and a power supply 250 disposed outside of (external to) cryostat 210. Superconducting magnet system 200 further includes a magnet controller 280 which may control various operations of superconducting magnet system 200.

Superconducting magnet system 200 further includes first and second electrically conductive leads 201 and 202 and third and fourth electrically conductive leads 203 and 204. Here, first and third electrically conductive leads 201 and 203 pass through vent 215. However, in other variations of superconducting magnet system 200 first and third electrically conductive leads 201 and 203 may pass through separate access openings in outer shell 211 and inner vessel 212.

First and second electrically conductive leads 201 and 202 are connected to each other at an electrical contact 205, and third and fourth electrically conductive leads 203 and 204 are connected to each other at an electrical contact 206. First and third electrically conductive leads 201 and 203 are connected to power supply 250. First electrically conductive lead 201 and/or third electrically conductive lead 203 may be connected to power supply 250 via a switch (not shown). Second and fourth electrically conductive leads 202 and 204 are connected to opposite ends of electrically conductive coil(s) 230. In some versions of superconducting magnet system 200, first and third electrically conductive leads 201 and 203 may be retractable from the outer shell 211 of cryostat 210 once electrically conductive coil(s) 230 are superconducting and persistent current switch 240 is operational. In some variations, first and second electrically conductive leads 201 and 202 may be replaced with one electrically conductive lead, and third and fourth electrically conductive leads 203 and 204 may be replaced with another electrically conductive lead, and electrical contacts 205 and 206 may be omitted.

Beneficially, superconducting magnet system 200 is a helium bath type system. In some embodiments, inner vessel 212 may contain a relatively small amount of cryogenic fluid compared to helium volumes in typical helium bath type systems, for example 50 to 100 liters (or less) of liquid helium.

Persistent current switch 240 is disposed within inner vessel 212 and may comprise a piece of superconductor wire connected across opposite ends of electrically conductive coil(s) 230 via second and fourth electrically conductive leads 202 and 204, attached to a small heater.

Superconducting magnet system 200 may have one or more sensors (not shown in FIG. 2) for measuring various operating parameters, such as temperatures, at various locations, levels of cryogenic fluid (e.g., liquid helium), whether components such as compressor 270 are properly operating, whether the power has been lost, for example due to an electrical power outage, etc. Each sensor may be connected to magnet controller 280 and supply a corresponding sensor signal to magnet controller 280.

Magnet controller 280 may comprise a processor and memory, including nonvolatile memory and volatile memory. The nonvolatile memory may store programming code or instructions (software) for causing the processor to execute one or more algorithms for controlling operations of superconducting magnet system 200.

As noted above, in some versions of superconducting magnet system 200, first and third electrically conductive leads 201 and 203 each may be retractable. In that case, during a startup operation of superconducting magnet system 200, retractable leads 201 and 203 are inserted into inner vessel 212 and the wire in persistent current switch 240 is heated above its transition temperature so that it becomes resistive. In some embodiments, first and third electrically conductive leads 201 and 203 may each have a protruding pin at an end thereof which may be received and coupled into a socket provided in each of electrical contacts 205 and 206.

Electrically conductive coil(s) 230 is/are initially energized by external power supply 250 passing a current through electrically conductive coil(s) 230. Since the wire in persistent current switch 240 is being heated during the startup operation, its resistance is substantially greater than that of electrically conductive coil(s) 230, so the current from the external power supply passes through electrically conductive coil 230.

To transition to operation in persistent mode, the current through electrically conductive coil(s) 230 is adjusted until the desired magnetic field is obtained, then the heater in persistent current switch 240 is turned off. After the heater is turned off, the superconductor wire in persistent current switch 240 cools to its superconducting temperature, short-circuiting electrically conductive coil(s) 230, which as mentioned above is also superconducting. The current in the power supply is ramped down and leads 201 and 203 are retracted from inner vessel 212.

Figure 3:
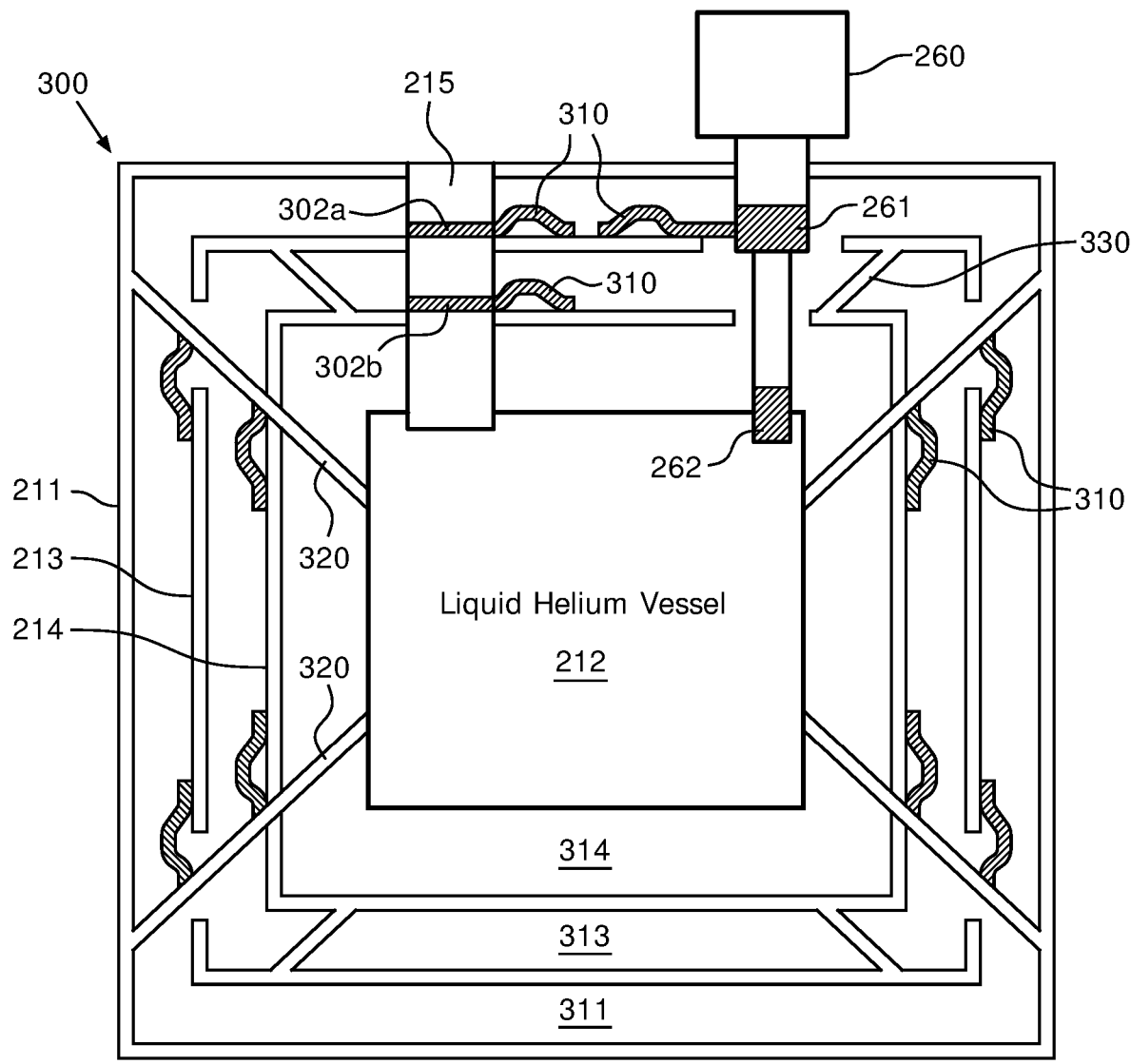
FIG. 3 illustrates a portion of first exemplary embodiment of a cryostat and a cold head.

FIG. 3 illustrates a portion of first exemplary embodiment of a cryostat 300 and cold head 260. In particular, cryostat 300 may be one embodiment of cryostat 210 in superconducting magnet system 200. It should be understood that, in general, cryostat 300 may include many other components which are not illustrated in FIG. 3. Some components have been omitted from FIG. 3 for clarity of illustration, and so as not to obscure aspects of the present invention to be discussed below.

Cryostat 300 includes outer shell 211 and: first thermal shield 213; second thermal shield 214; and inner vessel 212 all disposed within outer shell 211. Cryostat 300 also includes vent 215 and first and second heat exchangers 302*a* and 302*b*.

Cold head 260 is a two-stage cold head, including a first cooling stage 261 which is disposed within outer shell 211 and which is configured to provide cooling to a first temperature (e.g., a temperature in a range from about 35° K to about 85° K), and a second cooling stage 262 which is disposed within outer shell 211 and which is configured to contact the cryogenic fluid within inner vessel 212 and to cool the cryogenic fluid to a second temperature (e.g., about 4.2° K) which is less than the first temperature and which is sufficiently cold to condense a cryogenic gas (e.g., helium gas) to maintain the cryogenic fluid in a liquid state (e.g., liquid helium). Beneficially, cold head 260 is fixed to outer shell 211 of cryostat 300, for example by being welded to outer shell 211.

As can be seen in FIG. 3, first thermal shield 213 is disposed between inner vessel 212 and outer shell 211. In particular, first thermal shield 213 is disposed between second thermal shield 214 and outer shell 211, and second thermal shield 214 is disposed between inner vessel 212 and first thermal shield 213. A first vacuum space 311 is defined between first thermal shield 213 and outer shell 211; a second vacuum space 313 is defined between first thermal shield 213 and second thermal shield 214; and a third vacuum space is defined between second thermal shield 214 and inner vessel 212. Thus, first thermal shield 213 and second thermal shield 214 are thermally isolated from each other and from inner vessel 212 and outer shell 211.

First thermal shield 213 is thermally connected to first cooling stage 261 of cold head 260, for example by a high thermal conductivity connection 310, and is also thermally connected to first heat exchanger 302*a*, for example by another high thermal conductivity connection 310. Here, high thermal conductivity connections 310 may be rigid or flexible, and in some versions may comprise metallic connections, for example aluminum or copper straps. In some embodiments, high thermal conductivity connection 310 may have a thermal conductivity of >0.5 W/° K at operating temperatures of cryostat 300. Second thermal shield 214 is thermally connected to first heat exchanger 302*a*, for example by another high thermal conductivity connection 310. However, second thermal shield 214 is thermally isolated from cold head 260 and thus also may be referred to as a "floating shield." Thus the heat load on second thermal shield 214 is substantially reduced compared to first thermal shield 213 which is thermally connected to first stage 211 of cold stage 260. Therefore in the event of loss of refrigeration by cold head 260 (for example due to a loss off electrical power, or during transport of cryostat 300), the cold helium gas escaping through vent 215 may cool second thermal shield 214 via second heat exchanger 302b to a much cooler temperature, thereby greatly reducing the rate of helium loss.

In some versions of cryostat 300, first and second thermal shields 213 and 214 may each comprise an aluminum alloy or other material which can provide a high lateral thermal conductance and sufficient mechanical strength or rigidity to withstand the forces which may be induced in the event of a quench of the superconducting magnet.

Structurally, inner vessel 212 is supported from outer shell 211 with one or more first thermally isolating (i.e., low thermal conductivity) support elements 320 which physically connect(s) inner vessel 212 and outer shell 211 with each other. In this embodiment, second thermal shield 214 is mechanically fixed or attached to one or more of the first thermally isolating support elements 320, and first thermal shield 213 is in turn supported from second thermal shield 214 via one or more second thermally isolating support elements 330 which physically connect first thermal shield 213 and second thermal shield 214 to each other. Beneficially, first thermal shield 213 and second thermal shield 214 are also thermally coupled or attached to one or more of the first thermally isolating support elements 320, for example via one or more high thermal conductivity connections 310.

Beneficially, first thermally isolating support elements 320 and/or second thermally isolating support elements 330 may each have a thermal conductivity which is <0.04 W/° K at operating temperatures of cryostat 300. In some versions, first thermally isolating support elements 320 and/or second thermally isolating support elements 330 may be made of Kevlar, s-glass/epoxy, G-10, carbon fiber/epoxy, alumina, or other suitable low thermal conductivity material and sufficient mechanical strength at cryogenic temperatures, for example a material having a thermal conductivity which is less than 0.3 W/m ° K.

Other arrangements for structurally supporting inner vessel 212, first thermal shield 213, and second thermal shield 214 besides that shown in FIG. 3 are contemplated.

Figure 4:
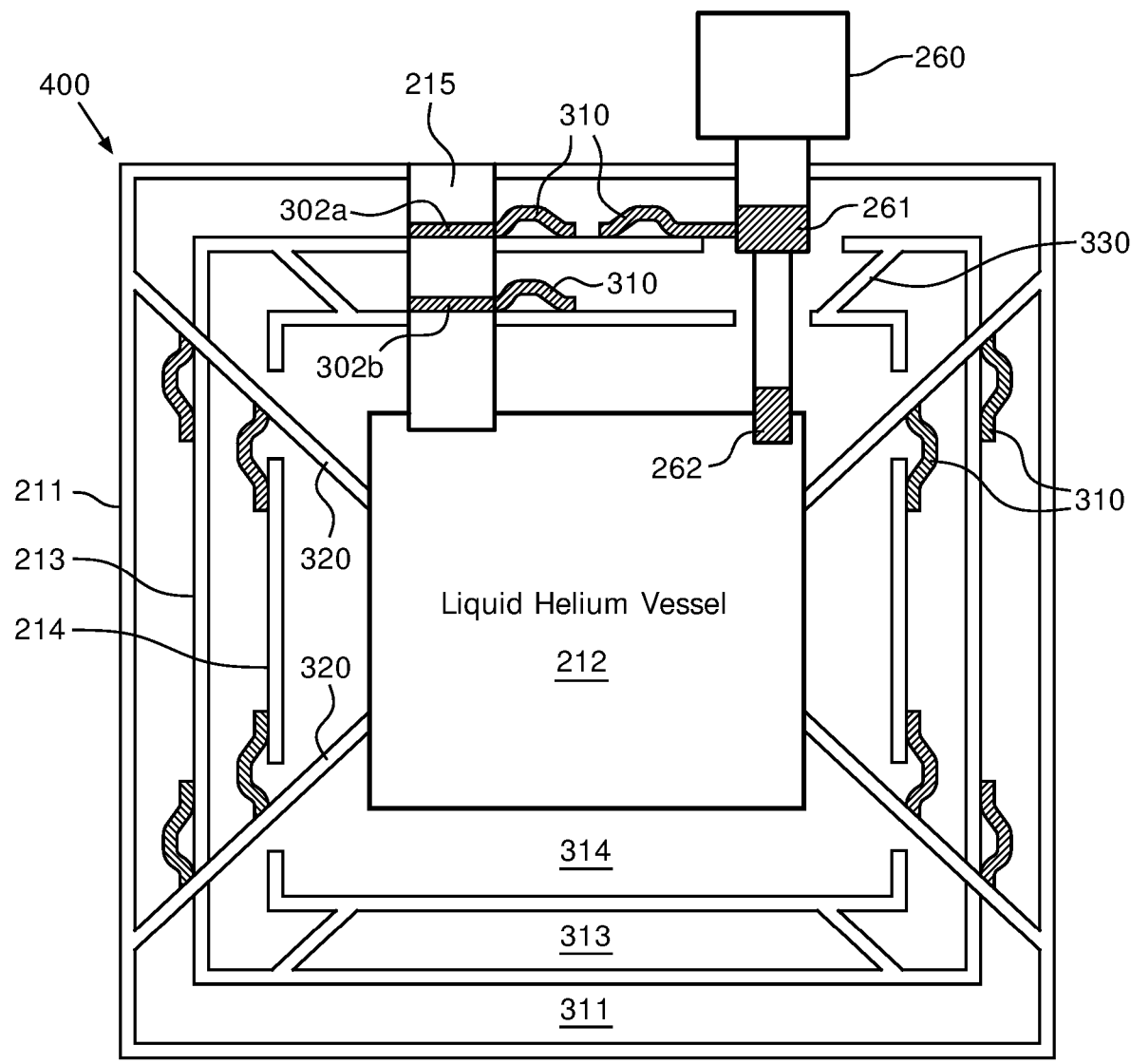
FIG. 4 illustrates a portion of second exemplary embodiment of a cryostat and a cold head.

For example, FIG. 4 illustrates a portion of second exemplary embodiment of a cryostat 400 and cold head 260. Cryostat 400 is similar to cryostat 300, so only the differences therebetween will be described. In particular, in cryostat 400 first thermal shield 213 is mechanically fixed or attached to one or more of the first thermally isolating support elements 320, and second thermal shield 214 is in turn supported from first thermal shield 213 via one or more second thermally isolating support elements 330 which physically connect first thermal shield 213 and second thermal shield 214 to each other. As in cryostat 300, in cryostat 400 first thermal shield 213 and second thermal shield 214 are also thermally coupled or attached to one or more of the first thermally isolating support elements 320, for example via one or more high thermal conductivity connections 310.

Figure 5:
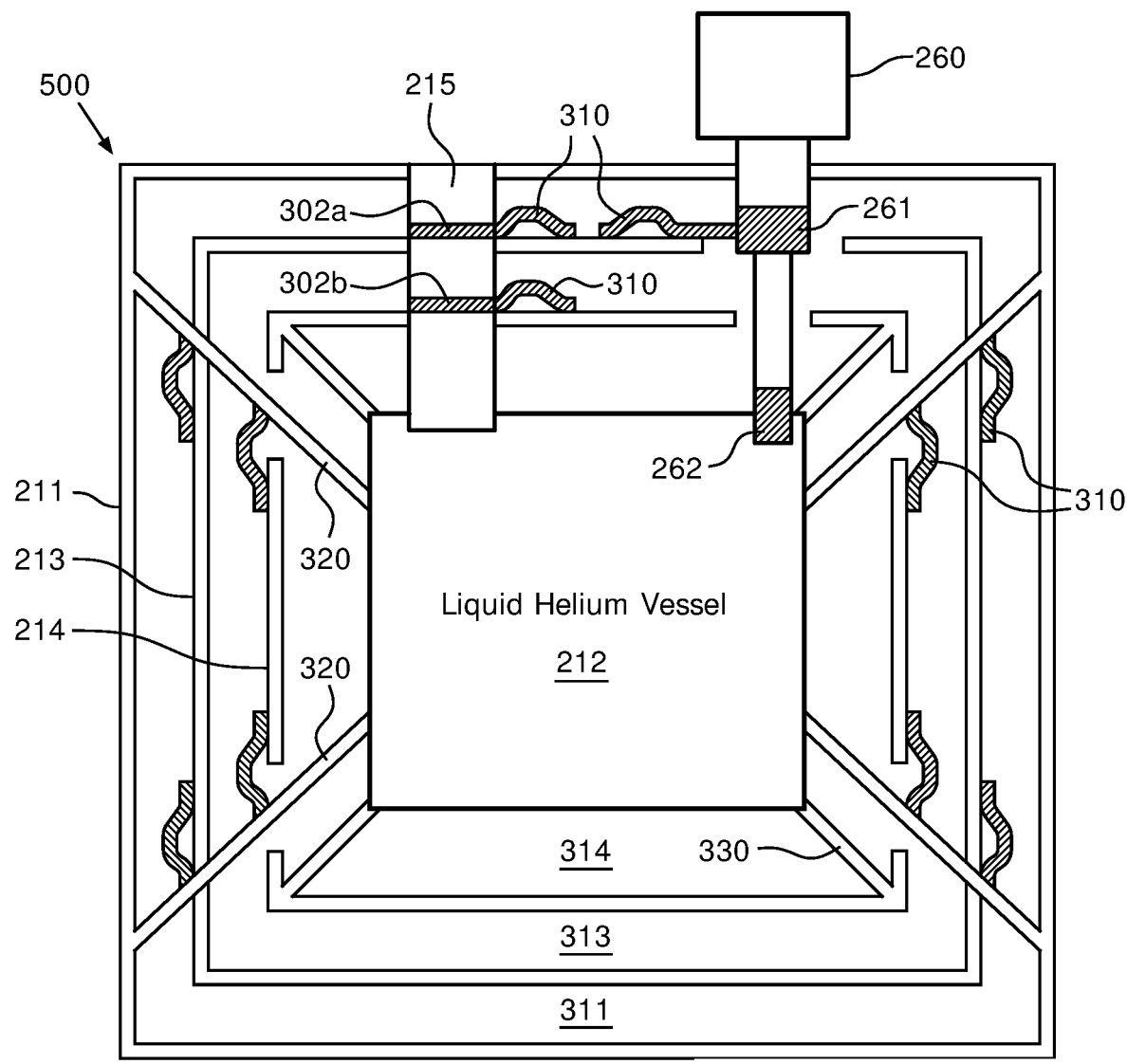
FIG. 5 illustrates a portion of third exemplary embodiment of a cryostat and a cold head.

FIG. 5 illustrates a portion of third exemplary embodiment of a cryostat 500 and cold head 260. Cryostat 500 is similar to cryostat 400, so only the differences therebetween will be described. In particular, in cryostat 500 first thermal shield 213 is mechanically fixed or attached to one or more of the first thermally isolating support elements 320, and second thermal shield 214 is supported from inner vessel 212 via one or more second thermally isolating support elements 330 which physically connect inner vessel 212 and second thermal shield 214 to each other. As in cryostats 300 and 400, in cryostat 500 first thermal shield 213 and second thermal shield 214 are also thermally coupled or attached to one or more of the first thermally isolating support elements 320, for example via one or more high thermal conductivity connections 310.

Other arrangements for structurally supporting inner vessel 212, first thermal shield 213, and second thermal shield 214 besides those shown in FIGS. 3-5 are contemplated. For example, some embodiments may include a modification of the support structure of cryostat 300 in FIG. 3, wherein at least one first thermally isolating support element physically connects the inner vessel and the second thermal shield to each other, at least one second thermally isolating support element physically connects the first thermal shield and the second thermal shield to each other, and at least one third thermally isolating support element physically connects the second thermal shield and the outer shell to each other.

While preferred embodiments are disclosed herein, many variations are possible which remain within the concept and scope of the invention. For example, embodiments have been described above in the context of a helium bath type system. However, in other embodiments, it is possible that the principles disclosed herein may be adapted to be employed in a "cryofree" or sealed system. Such variations would become clear to one of ordinary skill in the art after inspection of the specification, drawings and claims herein. The present invention therefore is not to be restricted except within the scope of the appended claims.

What is claimed is:
1. A magnetic resonance imaging (MRI) apparatus, comprising:
   a patient table configured to hold an associated patient;
   a superconducting electrically conductive coil configured to produce a magnetic field when an electrical current is passed therethrough;
   gradient coils configured to at least partially surround a portion of the patient for which the MRI apparatus generates an image;
   a radio frequency (RF) coil configured to apply an RF signal to the portion of a patient and to alter an alignment of the magnetic field;
   a sensor configured to detect changes in the magnetic field caused by the radio frequency signal and the patient;
   an outer shell;
   an inner vessel disposed within the outer shell, the inner vessel having disposed therein the superconducting electrically conductive coil and being configured to have a cryogenic fluid disposed therein;
   a cold head having: a first cooling stage which is disposed within the outer shell and which is configured to provide cooling to a first temperature, and having a second cooling stage which is disposed within the outer shell and which is configured to contact the cryogenic fluid within the inner vessel and cool the cryogenic fluid to a second temperature which is less than the first temperature;
   a vent extending from an interior of the inner vessel to an exterior of the outer shell, the vent having associated therewith a first heat exchanger and a second heat exchanger;
   a first thermal shield disposed between the inner vessel and the outer shell, the first thermal shield being thermally connected to the first cooling stage of the cold head and further being thermally connected to the first heat exchanger and being thermally isolated from the inner vessel and outer shell, wherein a first vacuum space is defined between the first thermal shield and the outer shell;

a second thermal shield disposed between the inner vessel and the first thermal shield, the second thermal shield being thermally connected to the second heat exchanger and being thermally isolated from the inner vessel, the outer shell, the first thermal shield, and the cold head, wherein a second vacuum space is defined between the first thermal shield and the second thermal shield, and a third vacuum space is defined between the first thermal shield and the inner vessel; and a plurality of thermally isolating support elements configured to attach the inner vessel, the outer shell, the first thermal shield, and the second thermal shield to each other.

2. The MRI apparatus of claim 1, wherein the plurality of thermally isolating support elements are made of one selected from Kevlar, s-glass/epoxy, G-10, carbon fiber/epoxy, and alumina.

3. The MRI apparatus of claim 1, wherein the plurality of thermally isolating support elements further comprise:
at least one first thermally isolating support element physically connecting the inner vessel, the second thermal shield, and the outer shell to each other; and
at least one second thermally isolating support element physically connecting the first thermal shield and the second thermal shield to each other,
wherein the first thermal shield and the second thermal shield are both thermally attached to the at least one first thermally isolating support element.

4. The MRI apparatus of claim 1, wherein the plurality of thermally isolating support elements further comprise:
at least one first thermally isolating support element physically connecting the inner vessel, the first thermal shield, and the outer shell to each other; and
at least one second thermally isolating support element physically connecting the first thermal shield and the second thermal shield to each other,
wherein the first thermal shield and the second thermal shield are both thermally attached to the at least one first thermally isolating support element.

5. The MRI apparatus of claim 1, wherein the plurality of thermally isolating support elements further comprise: at least one first thermally isolating support element physically connecting the inner vessel, the first thermal shield, and the outer shell to each other; and
at least one second thermally isolating support element physically connecting the first thermal shield and inner vessel to each other,
wherein the first thermal shield and the second thermal shield are both thermally attached to the at least one first thermally isolating support element.

6. The apparatus of claim 1, wherein the cold head is welded to the outer shell.

7. The apparatus of claim 1, wherein the inner vessel has the cryogenic fluid disposed therein as liquid helium.

8. The apparatus of claim 7, wherein a helium gas passes through the vent from the inner vessel to outside of the outer shell after a period of time when the cold head is not powered.

9. The apparatus of claim 1, wherein the first temperature is in a range of 35° K to 75° K, and the second temperature is below 5° K.

10. The apparatus of claim 1, wherein the plurality of thermally isolating support elements include at least one flexible support element.

11. An apparatus, comprising:
an outer shell;
an inner vessel disposed within the outer shell, the inner vessel having disposed therein an electrically conductive coil;
a cold head having a first cooling stage disposed within the outer shell, and having a second cooling stage disposed within the outer shell and configured to contact an interior space inside the inner vessel;
a vent extending from the interior of the inner vessel to an exterior of the vacuum shell, the vent having associated therewith a first heat exchanger and a second heat exchanger;
a first thermal shield disposed between the inner vessel and the outer shell, the first thermal shield being thermally connected to the first cooling stage of the cold head and further being thermally connected to the first heat exchanger and being thermally isolated from the inner vessel and outer shell; and
a second thermal shield disposed between the inner vessel and the first thermal shield, the second thermal shield being thermally connected to the second heat exchanger and being thermally isolated from the inner vessel, the outer shell, the first thermal shield, and the cold head.

12. The apparatus of claim 11, further comprising:
at least one first thermally isolating support element physically connecting the inner vessel, the second thermal shield, and the outer shell to each other; and
at least one second thermally isolating support element physically connecting the first thermal shield and the second thermal shield to each other.

13. The apparatus of claim 12, wherein the first thermal shield and the second thermal shield are both thermally attached to the at least one first thermally isolating support element.

14. The apparatus of claim 11, further comprising:
at least one first thermally isolating support element physically connecting the inner vessel, the first thermal shield, and the outer shell to each other; and
at least one second thermally isolating support element physically connecting the first thermal shield and the second thermal shield to each other.

15. The apparatus of claim 14, wherein the first thermal shield and the second thermal shield are both thermally attached to the at least one first thermally isolating support element.

16. The apparatus of claim 11, further comprising:
at least one first thermally isolating support element physically connecting the inner vessel, the first thermal shield, and the outer shell to each other; and
at least one second thermally isolating support element physically connecting the first thermal shield and inner vessel to each other.

17. The apparatus of claim 16, wherein the first thermal shield and the second thermal shield are both thermally attached to the at least one first thermally isolating support element.

18. The apparatus of claim 11, further comprising:
at least one first thermally isolating support element physically connecting the inner vessel and the second thermal shield to each other;
at least one second thermally isolating support element physically connecting the first thermal shield and the second thermal shield to each other; and at least one third thermally isolating support element physically connecting the second thermal shield and the outer shell to each other.

19. The apparatus of claim 11, further comprising:

at least one first thermally isolating support element physically connecting the inner vessel and the first thermal shield to each other;

at least one second thermally isolating support element physically connecting the first thermal shield and the second thermal shield to each other; and at least one third thermally isolating support element physically connecting the first thermal shield and the outer shell to each other.

20. The apparatus of claim 11, further comprising:

at least one first thermally isolating support element physically connecting the inner vessel and the first thermal shield to each other;

at least one second thermally isolating support element physically connecting the first thermal shield and the inner vessel to each other; and at least one third thermally isolating support element physically connecting the first thermal shield and the outer shell to each other.

\* \* \* \* \*